United States Patent [19]

Kurtz et al.

[11] 4,018,224
[45] Apr. 19, 1977

[54] UNDERWATER DRAINAGE DEVICE WITH DUAL COLLECTION CHAMBERS

[75] Inventors: Leonard D. Kurtz, Woodmere; Robert E. Bidwell, Melville, both of N.Y.

[73] Assignee: Deknatel, Inc., Long Island, N.Y.

[22] Filed: Apr. 7, 1976

[21] Appl. No.: 674,482

[52] U.S. Cl. .............................................. 128/276
[51] Int. Cl.² ...................................... A61M 1/00
[58] Field of Search ........................... 128/275–278

[56] References Cited

UNITED STATES PATENTS

| | | | |
|---|---|---|---|
| 3,363,626 | 1/1968 | Bidwell et al. | 128/276 |
| 3,683,913 | 8/1972 | Kurtz et al. | 128/276 |
| 3,757,783 | 9/1973 | Alley | 128/277 |
| 3,783,870 | 1/1974 | Schachet | 128/276 |
| 3,847,152 | 11/1974 | Schachet | 128/276 |
| 3,861,390 | 1/1975 | Schachet | 128/276 |

Primary Examiner—Robert W. Michell
Assistant Examiner—Henry S. Layton
Attorney, Agent, or Firm—Larson, Taylor & Hinds

[57] ABSTRACT

The present invention provides an underwater drainage apparatus which is adapted to be used for draining a body cavity. The underwater drainage device is provided with two collection chambers in addition to the usual water seal chamber and pressure regulating monometer. The two collection chambers intercommunicate so that the same vacuum is applied to both chambers but a spill over compartment is provided between the two collection chambers to prevent fluid collected in one chamber from passing into the other collection chamber.

6 Claims, 4 Drawing Figures

UNDERWATER DRAINAGE DEVICE WITH DUAL COLLECTION CHAMBERS

BACKGROUND OF THE INVENTION

1. Field of the Invention

This invention relates to surgical drainage systems and more particularly to an underwater drainage apparatus which is adapted to be connected to the pleural cavity of a patient for draining fluid and gases there from. The apparatus is of the type disclosed in U.S. Pat. Nos. 3,363,626 and 3,363,627 and in copending patent application Ser. No. 621,591 filed Oct. 10, 1975 for "Attachable Expansion Chamber for Pleural Drainage Device".

2. Background of the Invention

In the aforementioned U.S. Pat. Nos. 3,363,626 and 3,363,627 issued to Bidwell et al, issued Jan. 16, 1968, a general explanation of the purpose and function of an underwater drainage apparatus is setforth as well as giving a brief explanation of the lung structure and of the human breathing function.

Numerous other devices have been developed to maintain a vacuum in and to drain the pleural and thoracic cavities. In addition, numerous improvements have been made in the devices disclosed in the above-mentioned patents. For example, improvements are disclosed in U.S. Pat. Nos. 3,559,647; 3,783,870; 3,847,152; 3,853,128; and 3,809,085. The devices disclosed in all of the foregoing patents are generally classified as three chamber systems since they provide one chamber for collecting fluids drained from the body cavity, a chamber for maintaining a water seal on the collection chamber, and a chamber for regulating the amount of vacuum in the device.

In the above mentioned prior pending application Ser. No. 621,591 there is described a pleural drainage device of the three chamber type having an attachable fourth chamber which is adapted to serve as an additional collection chamber. As set forth in the copending application quite frequently it is desirable to connect more than one thoracotomy tube to the body cavity to be drained. For example, one thoracotomy tube could be connected to a low point in the pleural cavity which would collect most of the liquid from the cavity and another thoracotomy tube could be connected to a higher point in the cavity where some liquid together with gases could be removed. Prior to the use of the device disclosed in the prior application referred to, it was necessary to utilize two separate pleural drainage devices, one device being connected to the lower point in the pleural cavity and the other device being connected to the high point in the pleural cavity. Alternatively a single pleural drainage device could be used with the tube leading from the collection chamber having a Y connection so as to provide for connection to two thoracotomy tubes. However, it was not possible with such a device to determine the source of the liquid collected within the collection chamber.

Thus, there has been need for a drainage system which utilizes a single vacuum source and yet provides separate collection chamber for each thoracotomy tube. While the device disclosed in the prior patent application hereinbefore referred to, met some of these needs, it was found desirable to provide a single device previously assembled which provides two separate collection chambers and has an overfill chamber to indicate excessive drainage from the upper drainage site in the pleural cavity.

SUMMARY OF THE INVENTION

The present invention provides a surgical drainage system which has a pair of collection chambers utilizing the same source of suction. There is provided a single water seal chamber for both collection chambers and a single pressure manometer which indicates the degree of vacuum existing in both of the collection chambers. The drainage device is so designed that liquid from one of the collection chambers cannot pass through into the other collection chamber. The two chambers are separated by an overflow or spillover chamber. The overflow chamber permits liquid which has collected in the smaller collection chamber which would normally be connected with an upper location in the pleural cavity, to overflow into a separate chamber so as to indicate to the attending nurse or physician that a second device should be connected to the patient in order to prevent mixing of the fluids in the two collection chambers. The passageways between the two collection chambers are arranged so as to prevent the direct flow of fluids from the smaller collection chamber into the large collection chamber.

The entire device comprising the two collection chambers, the water seal chamber and the pressure manometer are formed as an integral unit which may be readily carried in one hand and is simple to attach to a patient. The device may be used as a conventional three chambered device by simply not opening the connection to the additional collection chamber.

These and other features and advantages of the present invention will become more fully apparent from the detailed description of the preferred embodiment of the invention found herein below.

DETAILED DESCRIPTION OF PREFERRED EMBODIMENT

Figure 1:
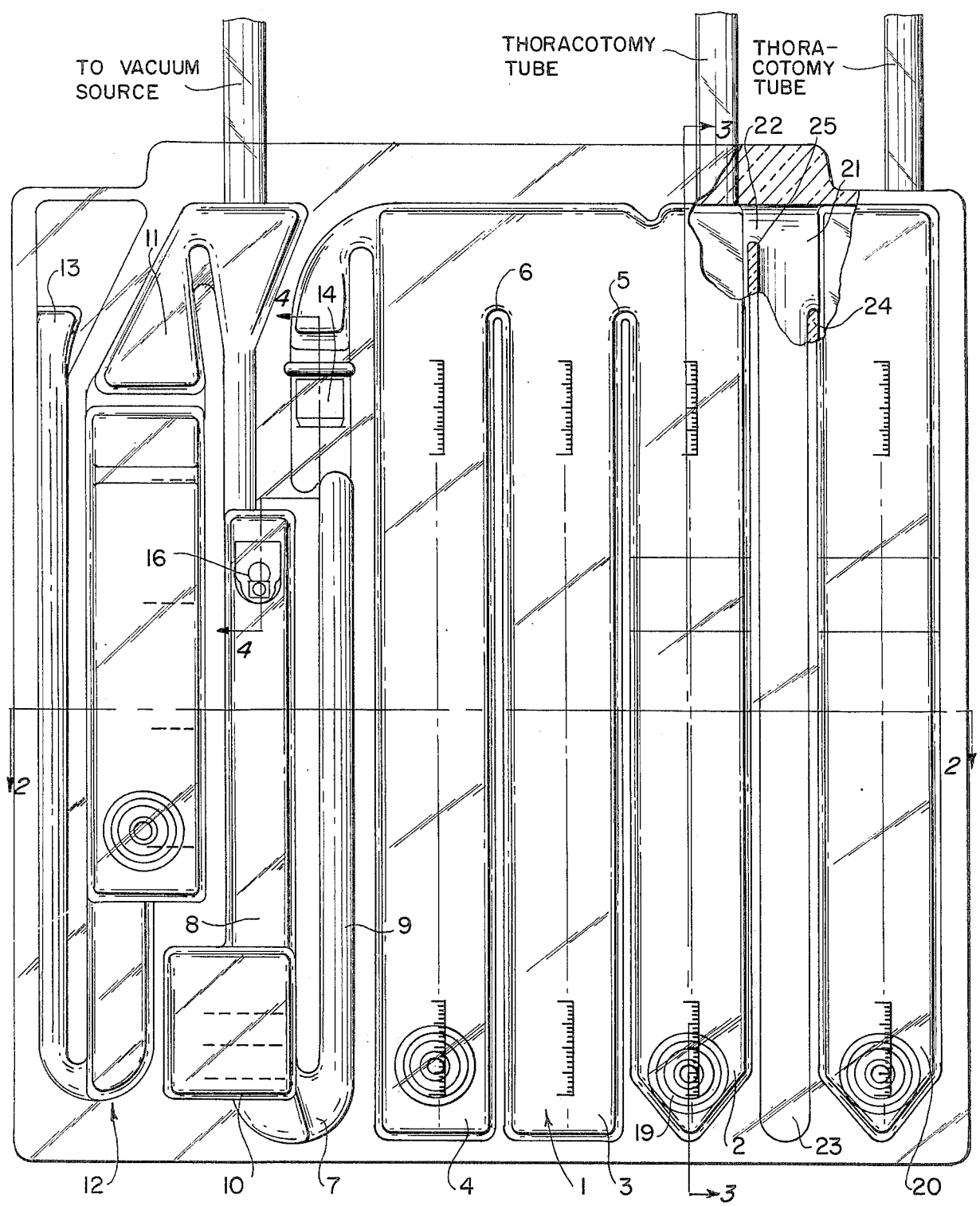
FIG. 1 is a front elevational view of a drainage system according to the present invention showing a pair of separate collection chambers.
Figure 2:
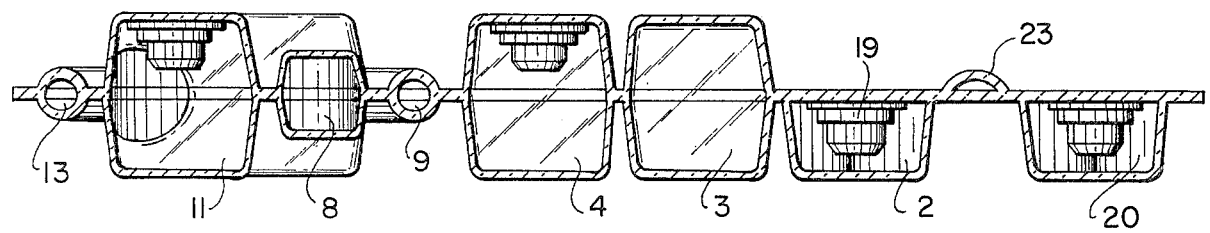
FIG. 2 is a cross sectional view along the line 2—2 of FIG. 1.
Figure 3:
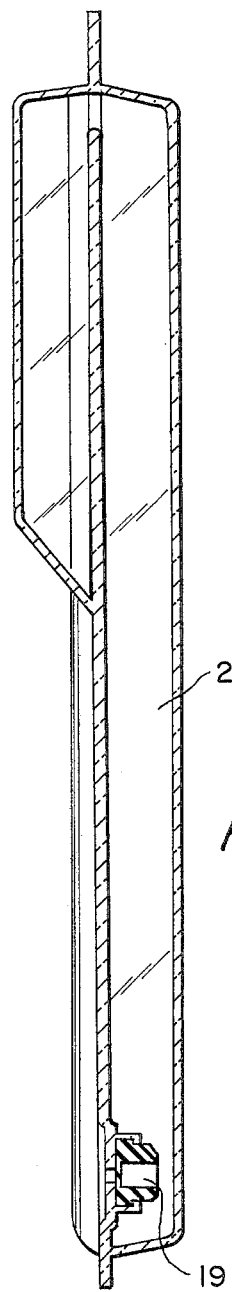
FIG. 3 is a sectional elevational view along the line 3—3 FIG. 1.

With reference now more specifically to the drawing wherein like numerals indicate like parts throughout the several views, a drainage system for collecting fluids and gases drained from a pleural cavity is shown. The mode of construction and operation of the main collection chamber, the water seal chamber and the pressure manometer chamber are essentially as disclosed in the prior patents hereinbefore referred to. However, the more fully describe the device disclosed in the drawings there is provided a main collection chamber 1 which is provided with internal partitions forming individual compartments 2, 3, and 4. The inlet to the main collection chamber is through an opening in the upper wall of the collection device, this opening being located substantially directly above compartment 2. Thus, as liquid flowing through the thoracotomy tube fills compartment 2, the liquid overflows the partition 5 and flows into the next compartment 3. When the compartment 3 is filled the liquid overflows the partition 6 and collects in compartment 4.

The water seal chamber comprises a U tube 7 having a large arm 8 and a small arm 9. The water which is to form the water seal fills the lower end portions of the small and large arm and partially fills the enlarged volume 10 within the lower end portion of the large arm 8. The upper end of the large arm 8 of the water seal chamber connects with the upper end of the large arm 11 of the pressure manometer 12. The small arm 13 of the pressure manometer has the upper thereof open to atmosphere.

There is provided in the upper end of the pleural drainage device between the arm 8 of the water seal and the arm 11 of the pressure manometer an opening (not shown) for connecting the device with a vacuum source.

Within the upper end of the small arm 9 of the water seal chamber there is provided a valve 14 which is more clearly shown in F 4. A partition 15 with an aperture therein is disposed within the arm 9 of the water seal chamber directly above the valve 14 and the valve is designed to prevent the flow of water from the water seal chamber into the main collection chamber during periods of high negativity within the pleural cavity. As the water in the water seal chamber rises in the small arm 9 and reaches the valve 14, the valve will be raised so as to close off the opening in the partition 15 to prevent the water from passing on up through the upper end of the arm 9 and into the main collection chamber. The details of construction of this valve 14 and the specific manner in which it operates are more clearly disclosed in prior U.S. Pat. No. 3,683,913.

Figure 4:
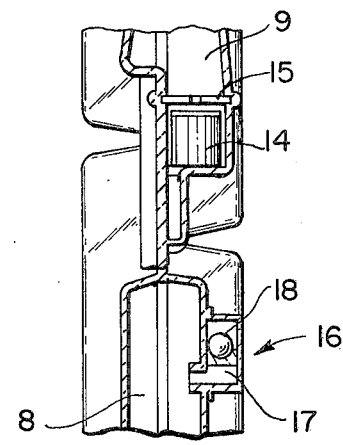
FIG. 4 is a partial sectional view along the line 4—4 of FIG. 1.

There is provided a valve 16 in the upper end of the large arm 8 of the water seal chamber. This valve is also disclosed in greater detail in FIG. 4. This valve performs the same function as the valve disclosed in U.S. Pat. No. 3,853,128, that is, it prevents the buildup of high positive pressures within the pleural cavity. A passageway 17 interconnects the interior of the large arm 8 of the water seal chamber with atmosphere through a one way ball valve 18. When the pressure within the drainage device exceeds atmospheric pressure the ball valve 18 will rise on its seat and permit the escape of gases from within the drainage device. This prevents the buildup of any positive pressures within the pleural cavity resulting from some malfunction of the device.

Within the lower ends of the compartment 2 and 4 of the main collection chamber 1 and within the large arm 11 of the pressure manometer there are provided rubber diaphragms such as the diaphragm 19 shown in compartment 2. This diaphragm permits the insertion of a needle to sample the fluid within the chamber without interrupting the operation of the device.

The second or minor collection chamber is shown at 20. This collection chamber has an opening in the upper end thereof which is adapted to be connected with a thoracotomy tube which may in turn be connected with a location in the pleural cavity spaced from the location at which the thoracotomy tube extending from the other collection chamber is connected. Generally speaking, the main collection chamber 1 would be connected with the lower portion of the pleural cavity as it is from this area that most of the liquids will be drained, thus requiring a collection chamber of larger capacity. However, in many cases it is desirable to remove the gases and liquids which may collect in the upper portion of the pleural cavity and in such case the second collection chamber 20 may be utilized. The upper end of the collection chamber 20 has the side thereof open as at 21 to provide an interconnecting passageway through a smaller opening 22 with the main collection chamber 1. Thus, pressure conditions existing within the collection chamber 1 will also be present within the collection chamber 20 and, of course, the same pressure conditions will also exist within the pleural cavity at the points to which the separate thoracotomy tubes are connected.

Between the compartment 2 of collection chamber 1 and collection chamber 20 there is provided a spillover or overflow chamber 23. It can be seen that as the liquid fills chamber 20 it will overflow the upper end of partition 24 and flow into the overflow chamber 23. The upper end 25 of the partition separating overflow chamber 23 and compartment 2 of collection chamber 1 is located at a higher point than the upper end 24 of the partition separating the overflow chamber 23 from collection chamber 20. Thus, liquid is prevented from flowing directly from chamber 20 into compartment 2 of collection chamber 1.

The general operation of a pleural drainage device as disclosed herein is described in detail in the aforementioned patents. Usually, an underwater drainage device is connected through a thoracotomy tube to a low point in the thoracic cavity. If it is also desired at that time or at a later time to connect a high drain to the thoracic cavity, a second thoracotomy tube may be connected from the chamber 20 to the high point in the cavity. The vacuum maintained within the collection chamber 20 will be the same as the vacuum maintained within the main collection chamber 1 by reason of the intercommunication between these two collection chambers. As the collection chamber 20 fills with liquid the liquid will overflow into the overflow chamber 23, thus providing an indication that the device should be replaced in order to prevent the liquid within the collection chamber 20 mixing with liquid within the collection chamber 1. Alternatively, the minor collection chamber could be emptied through the rubber diaphragm at the lower end of the chamber 20.

From the above description it can be seen that an underwater drainage apparatus has been provided which permits drainage from selected points in a pleural cavity so that the liquids will be separately collected and measurable in a single device having a single source of suction. Although the invention has been described in detail with respect to one embodiment thereof, it will be understood by those of ordinary skill in the art that variations and modifications may be effected within the scope and spirit of the invention.

We claim:

1. An underwater drainage device comprising, in combination,
    a main collection chamber
    having an inlet adapted to be connected to a pleural cavity,
    an outlet from the main collection chamber,
    a U-shaped water seal chamber
    a U-shaped manometer chamber,
    the upper end of one arm of the U-shaped water seal chamber being connected to the outlet from the main collection chamber,
    the upper end of the other arm of the U-shaped water seal chamber being connected to the upper end of one arm of the U-shaped manometer chamber, the other arm of the U-shaped manometer chamber being open to atmosphere, a connection from said device with a source of suction, during normal operation the source of suction maintaining the pleural cavity at a negative pressure determined by the fluid in the manometer chamber, a secondary collection chamber having another inlet adapted to be connected to a plural cavity, a passageway interconnecting the main collection chamber and the secondary collection chamber, and an overflow chamber being disposed between the secondary collection chamber and the main collection chamber.

2. An underwater drainage device according to claim 1 wherein the secondary collection chamber is integrally formed with the main collection chamber.

3. An underwater drainage device according to claim 1 wherein the passageway between the main collection chamber and the secondary collection chamber comprises an inlet from the secondary collection chamber into the overflow chamber and a connecting opening between the overflow chamber and the main collection chamber.

4. An underwater drainage device according to claim 3 wherein the lower edge of the inlet from the secondary collection chamber into the overflow chamber is spaced a substantial distance below the lower edge of the connecting opening between the overflow chamber and the main collection chamber.

5. An underwater drainage device according to claim 1 wherein the secondary collection chamber is integrally formed with the main collection chamber and is disposed on that side of the main collection chamber opposite to the water seal chamber.

6. An underwater drainage device according to claim 5 wherein the passageway between the main collection chamber and the secondary collection chamber comprises a relatively large inlet from the secondary collection chamber into the overflow chamber and a relatively small connecting opening between the overflow chamber and the main collection chamber.

* * * * *